(12) United States Patent
He et al.

(10) Patent No.: US 10,556,868 B2
(45) Date of Patent: Feb. 11, 2020

(54) METHOD FOR SYNTHESIZING 3-(DIFLUOROMETHYL)-1-METHYL-1H-PYRAZOLE-4-CARBOXYLIC ACID AND INTERMEDIATES THEREOF

(71) Applicant: ZHEJIANG YONGTAI TECHNOLOGY CO., LTD., Zhejiang (CN)

(72) Inventors: Renbao He, Zhejiang (CN); Yingmei Wang, Zhejiang (CN); Hongming Shao, Zhejiang (CN); Yizhong Jin, Zhejiang (CN)

(73) Assignee: ZHEJIANG YONGTAI TECHNOLOGY CO., LTD., Zhejiang (CN)

( * ) Notice: Subject to any disclaimer, the term of this patent is extended or adjusted under 35 U.S.C. 154(b) by 0 days.

(21) Appl. No.: 16/325,717

(22) PCT Filed: Sep. 29, 2016

(86) PCT No.: PCT/CN2016/100717
§ 371 (c)(1),
(2) Date: Feb. 14, 2019

(87) PCT Pub. No.: WO2018/032586
PCT Pub. Date: Feb. 22, 2018

(65) Prior Publication Data
US 2019/0202791 A1   Jul. 4, 2019

(30) Foreign Application Priority Data
Aug. 15, 2016 (CN) .......................... 2016 1 0668266

(51) Int. Cl.
C07D 231/28 (2006.01)
C07D 231/14 (2006.01)

(52) U.S. Cl.
CPC .......... *C07D 231/28* (2013.01); *C07D 231/14* (2013.01)

(58) Field of Classification Search
CPC .................................................. C07D 231/28
See application file for complete search history.

(56) References Cited

U.S. PATENT DOCUMENTS 7,994,341 B2 * 8/2011 Tobler .................. C07D 231/14
548/365.1

FOREIGN PATENT DOCUMENTS

CN      101962363       2/2011
CN      104945325       9/2015
(Continued)

OTHER PUBLICATIONS

Giornal et al., "A New Synthesis and Process Development of Bis(fluoroalkyl)pyrazoles as Novel Agrophores", Organic Process Research & Development, Apr. 15, 2014, pp. 1002-1009.
(Continued)

*Primary Examiner* — Golam M Shameem
(74) *Attorney, Agent, or Firm* — JCIP Global Inc.

(57) ABSTRACT

The present invention relates to a method for synthesizing a compound of 3-(difluoromethyl)-1-methyl-1h-pyrazole-4-carboxylic acid, wherein including the steps of:

(A) the diethyl ester compounds represented by the following Formula IV are reacted under the action of amine, alkali and carbonyl reagents to produce the acrylic diester compound represented by the following Formula I,

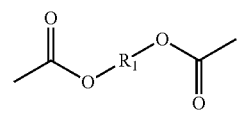

wherein:

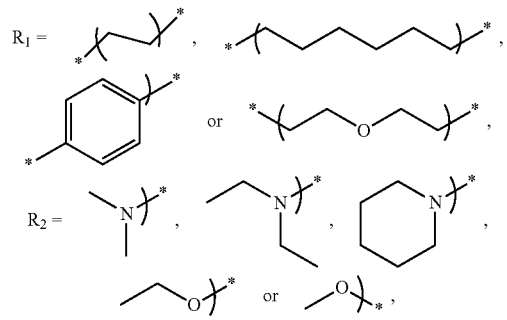

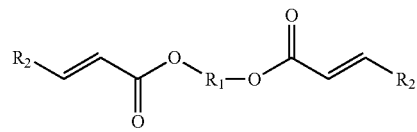

(B) the above compound represented by the Formula I is reacted with a fluoride reagent, a Lewis acid and a methyl hydrazine to form a pyrazole ring-containing diester compound represented by the Formula II,

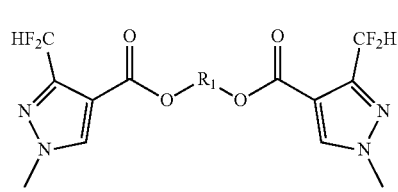

(C) the heterocyclic-containing diester compound represented by the Formula II is reacted with a base to give
(Continued)

3-(difluoromethyl)-1-methyl-1h-pyrazole-4-carboxylic acid represented by the Formula III.

11 Claims, No Drawings

(56) References Cited

FOREIGN PATENT DOCUMENTS

| | | |
|---|---|---|
| CN | 106279025 | 1/2017 |
| CN | 106366008 | 2/2017 |
| EP | 0569505 | 11/1993 |
| WO | 92/12970 | 8/1992 |
| WO | 2005/044804 | 5/2005 |
| WO | 2008/152138 | 12/2008 |

OTHER PUBLICATIONS

"International Search Report (Form PCT/ISA/210)", dated May 22, 2017, with English translation thereof, pp. 1-10.

* cited by examiner

METHOD FOR SYNTHESIZING 3-(DIFLUOROMETHYL)-1-METHYL-1H-PYRAZOLE-4-CARBOXYLIC ACID AND INTERMEDIATES THEREOF

CROSS-REFERENCE TO RELATED APPLICATION

This application is a 371 application of International PCT application serial no. PCT/CN2016/100717, filed on Sep. 29, 2016, which claims the priority benefit of Chinese application no. 201610668266.2, filed on Aug. 15, 2016. The entirety of each of the abovementioned patent applications is hereby incorporated by reference herein and made a part of this specification.

BACKGROUND

Technical Field

The present invention relates to a method for synthesizing a compound of 3-(difluoromethyl)-1-methyl-1h-pyrazole-4-carboxylic acid, and further relates to an intermediate acrylic diester compounds for synthesizing the compound and its preparation method; and also relates to another intermediate containing a pyrazole ring diester compound and its preparation method.

Description of Related Art 3-(difluoromethyl)-1-methyl-1h-pyrazole-4-carboxylic acid, cas: 17669-34-9, the structural formula is represented by the Formula III:

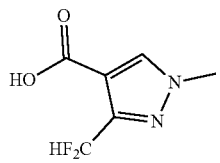

III

WO 92/12970 disclosed 3-(difluoromethyl)-1-methyl-1h-pyrazole-4-carboxylic acid and its use as a fungicide. These compounds are prepared starting from 4,4-difluoroacetoacetate, and the 4,4-difluoroacetoacetate are sequentially reacted with triethyl orthoformate and methyl hydrazine to give 3-(Difluoromethyl)-1-methyl-1h-pyrazole-4-carboxylic acid ester, and the carboxylic acid ester is then hydrolyzed to the carboxylic acid.

The fluoromethyl substituted heterocyclic carboxylic acid esters, including 3-(dimethyl)-1-methyl-1h-pyrazole-4-ethyl formate, and the method of preparing them by halogen exchange on the corresponding carboxylic acid esters of the chloromethyl substituted heterocyclic were disclosed by patent WO 2005/044804.

N,N-dimethyl tetrafluoride was reacted with ethoxy acrylate and methyl hydrazine to obtain 3-(dimethyl)-1-methyl-1h-zolpidem-4-carboxylic acid ester, and the carboxylic acid ester is then hydrolyzed to the carboxylic acid, which was disclosed by patent WO 2008/152138.

Org. Process res. Dev. 2014, 18, 1002-1009 described the reaction of N,N-dimethyl tetrafluoro ethylamine with dimethylamino acrylate and methyl hydrazine to give a fluoromethyl substituted carboxylic acid ester, The carboxylic acid ester was then hydrolyzed to the corresponding carboxylic acid to obtain 3-(dimethyl)-1-methyl-1h-zolpidem-4-carboxylic acid.

In the prior art, the method for preparing a 3-difluoromethyl-substituted pyrazole compound has a low yield, or the raw material structure is complicated and expensive. Alternatively, the introduction of a difluoromethyl group using a reagent based on hydrogen fluoride or fluoride may have toxicological problems or complicate industrialization due to its corrosive nature.

SUMMARY

The present invention provides a simple and efficient method for preparing 3-(difluoromethyl)-1-methyl-1h-pyrazole-4-carboxylic acid represented by Formula III:

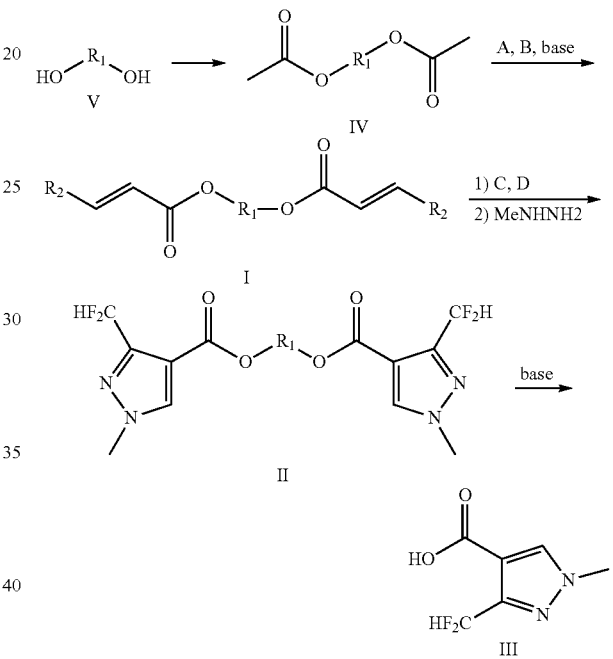

By reacting the acrylic diester compound (I) with a fluoride reagent or methyl hydrazine, a high yield of the intermediate pyrazole cyclic diester (compound II) can be obtained by the dual action of intramolecular ortho-group interaction and space action, and then the compound III can be obtained by hydrolysis.

Therefore, according to an embodiment of the present invention, the purpose of the present invention is to provide a synthesis method of 3-(dimethyl)-1-methyl-1h-zolpidem-4-carboxylic acid represented by the following Formula III,

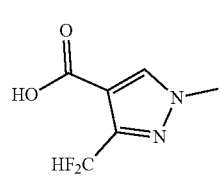

III

The method including the steps of:
(A) The diethyl ester compounds represented by the following Formula IV are reacted under the action of amine, alkali and carbonyl reagents to produce the acrylic diester compound represented by the following Formula I,

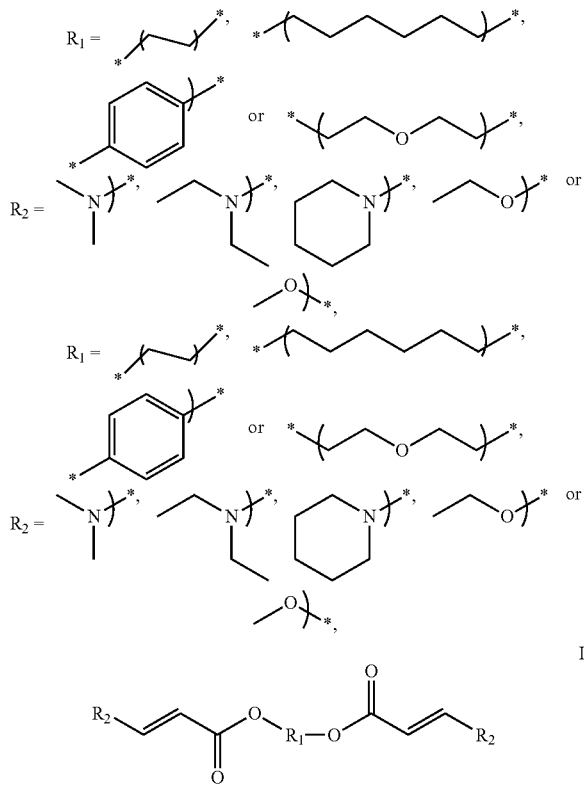

Wherein the definition of R₁ is the same as above;

(B) The above compound represented by the Formula I is reacted with a fluoride reagent, a Lewis acid and methyl hydrazine to form a pyrazole ring-containing diester compound represented by the following Formula II,

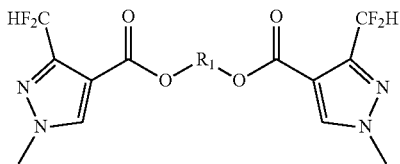

Wherein the definition of R₁ is the same as above;

(C) The heterocyclic-containing diester compound represented by the Formula II is reacted with a base to give 3-(difluoromethyl)-1-methyl-1h-pyrazole-4-carboxylic acid represented by the Formula III.

According to an embodiment of the present invention, wherein R₁ is

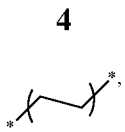

R₂ is

According to an embodiment of the present invention, the base in the step (C) is an organic base or an inorganic base. The organic base is trimethylamine, triethylamine, ethylenediamine, triisopropanolamine, tripropylamine, imidazole, benzimidazole, 2-fluoropyridine, 4-dimethylaminopyridine, methyl pyridine, pyrazine. Or n-methyl diphenyl ethylamine, preferably trimethylamine or triethylamine; the inorganic base is an alkali metal carbonate or an alkali metal hydroxide, preferably sodium carbonate, potassium carbonate, sodium hydroxide or potassium hydroxide, more preferably, sodium hydroxide.

According to one embodiment of the present invention, wherein the step (C) is carried out in the presence of a solvent which is water or methanol.

According to an embodiment of the present invention, wherein the reaction temperature in the step (C) is 40 to 80° C., preferably 60° C.; and the reaction time is 4 to 8 hours, preferably 4 hours.

According to an embodiment of the present invention, the molar ratio of the heterocyclic-containing diester compound represented by the Formula II to the base in the step (C) is from 1:1.0 to 1.2.

Accordingly, another object of the present invention is to provide an acrylic diester compound which can be used for the preparation of a 3-difluoromethyl substituted pyrazole compound, which avoiding the use of corrosive fluorine reagents and minimizing the yield loss of intermediate treatment and purification process. It is easy to achieve industrial production.

According to an embodiment of the present invention, the present invention provides an acrylic diester compound represented by the Formula I,

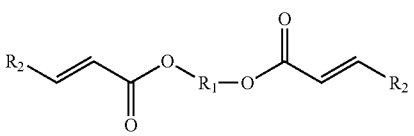

Wherein,

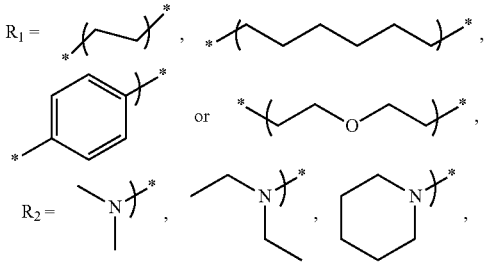

-continued

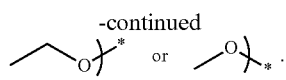

According to an embodiment of the present invention, the present invention provides an acrylic diester compound represented by the Formula I, wherein, $R_1$ is

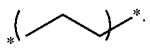

According to an embodiment of the present invention, the present invention provides an acrylic diester compound represented by the Formula I, wherein, $R_2$ is

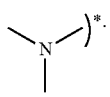

According to an embodiment of the present invention, the present invention provides an acrylic diester compound represented by the Formula I, wherein, $R_1$ is

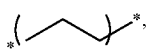

$R_2$ is

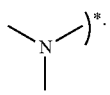

According to an embodiment of the present invention, the present invention provides an acrylic diester compound represented by the Formula I, wherein, $R_1$ is

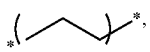

$R_2$ is

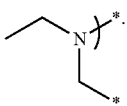

According to an embodiment of the present invention, this invention provides a method for the preparation of acrylic diester compounds represented by the Formula I,

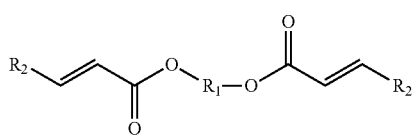

I

Wherein,

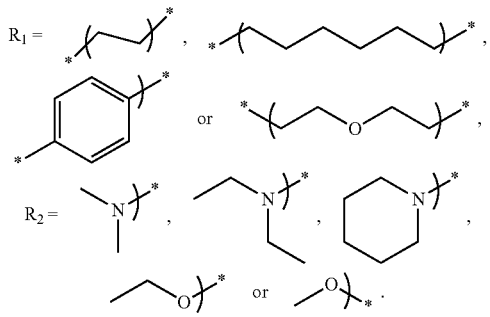

The method includes the steps of reacting diethyl ester compounds (IV) to form acrylic diester compounds (I) under the action of amine, alkali and carbonyl reagents.

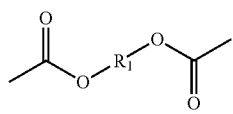

IV

Wherein,

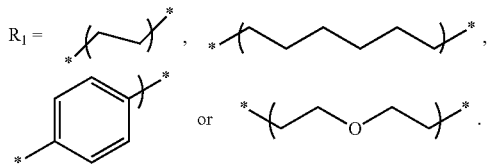

According to an embodiment of the present invention, this invention provides a method for the preparation of acrylic diester compounds represented by the Formula I, The method including the steps of:

(A1) the diethyl ester compound (IV) reacts with the carbonylating agent under the action of a base;

(A2) the reaction liquid obtained after the reaction of the step (1) is reacted with an amine to obtain an acrylic diester compound represented by the Formula I.

According to one embodiment of the invention, the amine in the preparation of the acrylic diester compound represented by the Formula I is selected from methylamine, dimethylamine, ethylamine, diethylamine, cyclohexylamine, piperidine, morpholine, dimethylamine hydrochloride, diethylamine hydrochloride, cyclohexylamine hydrochloride or piperidine hydrochloride, preferably, dimethylamine hydrochloride is used.

According to one embodiment of the invention, in the preparation of the acrylic diester compound represented by the Formula I, the base is selected from sodium methoxide, sodium ethoxide, sodium t-butoxide, potassium t-butoxide, sodium hydride or potassium hydride, preferably, sodium t-butoxide.

According to one embodiment of the invention, the carbonylating agent in the preparation of the acrylic diester compound represented by the Formula I is selected from carbon monoxide, methyl formate, ethyl formate, trimethyl orthoformate or triethyl orthoformate, preferably, carbon monoxide or ethyl formate.

According to one embodiment of the invention, the reaction (including the step (A1) and the step (A2)) in the preparation of the acrylic diester compound represented by the Formula I is carried out in a solvent, and the solvent is selected from toluene, methanol, ethanol, DMF or tetrahydrofuran, preferably, toluene.

According to one embodiment of the invention, in the preparation of the acrylic diester compound, the ratio of the amount of the diethyl ester compound, the carbonylating agent, the base, and the amine is 1:1.0-1.1:1.0-1.1:1.0-1.1.

According to one embodiment of the invention, in the preparation of the acrylic diester compound represented by the Formula I, the carbonylating agent is methyl formate, ethyl formate, trimethyl orthoformate or triethyl orthoformate. The reaction temperature of the step (A1) and the step (A2) is 10° C. to 50° C., preferably 20° C. to 25° C.

According to one embodiment of the invention, in the preparation of the acrylic diester compound represented by the Formula I, the carbonylating agent is carbon monoxide, the reaction temperature of the step (A1) is 50° C. to 80° C., preferably 60° C., the reaction pressure is 15 bar to 25 bar, preferably 20 bar; and the reaction temperature of the step (A2) is 10° C. to 50° C., preferably 20° C. to 25° C.

According to one embodiment of the invention, in the preparation of the acrylic diester compound represented by the Formula I, the diethyl ester compound represented by the formula IV is subjected to an addition reaction under the action of a base and a carbonylating agent at 10° C. to 50° C., the obtained intermediate reaction solution is subjected to an addition reaction with amine at 10° C. to −50° C., after completion of the reaction, the reaction solution is separated and purified to obtain an acrylic acid diester compound represented by the Formula I. The carbonylating agent is ethyl formate or triethyl orthoformate, preferably ethyl formate; the temperature of the two addition reactions is 10-50° C., preferably 20° C., and the reaction time in both steps is 8-24 hours. The ratio of the amount of the diethyl ester compound, the carbonylating agent, the base, and the amine is 1:1.0-1.1:1.0-1.1:1.0-1.1.

According to one embodiment of the invention, in the preparation of the acrylic diester compound represented by the Formula I, under the action of alkali, diethyl ester compounds and carbonyl reagents react in the high pressure reactor, the reaction pressure is 15-25 bar, preferably, 20 bar; the pressurized reaction time is 3-8 hours, preferably, 4 hours; and the reaction temperature is 50-80° C., preferably, 60° C.; the reaction fluid is added to the solution of amine and continues to participate in the reaction, the reaction temperature is 10-50° C., the reaction time is 1-8 hours, preferably, 2 hours. At the end of the reaction, the reaction fluid was separated and purified to obtain the acrylic diester compounds represented by the Formula I. The carbonyl reagent is a carbon monoxide gas. The ratio of the amount of the diethyl ester compound, the base, and the amine is from 1:1.0 to 1.1:1.0 to 1.1.

A further object of the present invention is to provide a diazole compound containing a pyrazole ring, this compound can be used to prepare pyrazole compounds substituted by 3-difluoromethyl, the preparation method of the compound avoid the use of corrosive fluorine reagents and minimize the yield loss of intermediate treatment and purification process. It is easy to achieve industrial production.

According to one embodiment of the invention, the present application provides a diazole compound containing a pyrazole ring represented by the Formula II.

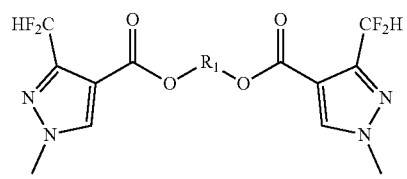

wherein, $R_1$ is

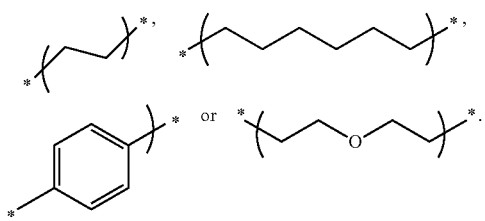

According to one embodiment of the invention, the present application provides a diazole compound containing a pyrazole ring represented by the Formula II.

Wherein, $R_1$ is

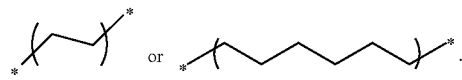

According to one embodiment of the invention, the present application provides a diazole compound containing a pyrazole ring represented by the Formula II.

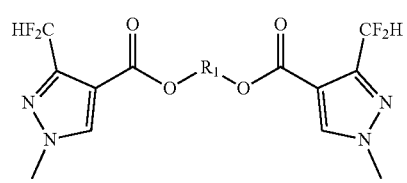

Wherein, $R_1$ is

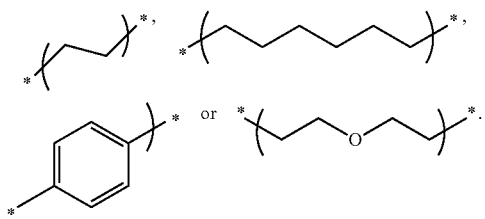

The method includes reacting compound I with a fluoride reagent, a Lewis acid, and a methyl hydrazine, the structure of compound I is as follows:

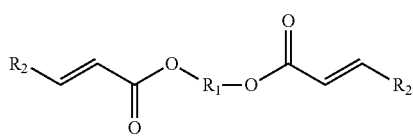

Wherein,

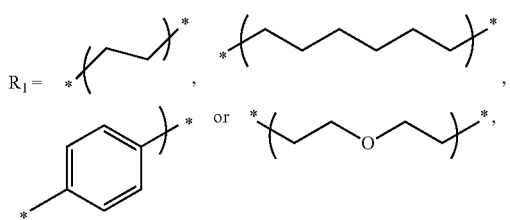

preferably, $R_1$ is

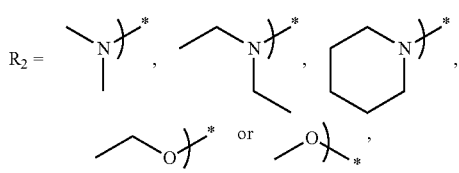

preferably, $R_2$ is

According to one embodiment of the invention, wherein,

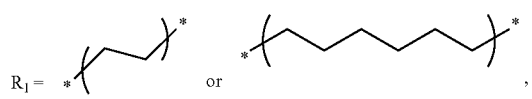

$R_2$ is

According to one embodiment of the invention, the present application provides a method for preparing a pyrazole ring-containing diester compound represented by the Formula II, including the steps of:

(B1) acrylic diester compounds represented by the Formula I react with fluoride reagents and Lewis acid in solvents;

(B2) the reaction product obtained in step (1) reacts with methyl hydrazine to produce diester compound which containing heterocyclic represented by the Formula II.

According to one embodiment of the invention, the fluoride reagent in the preparation of the pyrazole ring-containing diester compound of formula II is selected from N,N-dimethyl tetrafluoro ethylamine, difluoroacetyl fluoride or difluoroacetyl chloride, preferably, N,N-dimethyl tetrafluoro ethylamine.

According to one embodiment of the invention, the Lewis acid described in the preparation of the pyrazole ring-containing diester compound of formula II is boron trifluoride etherate.

According to one embodiment of the invention, the solvents of the step (B1) are dichloromethane, ethyl ether, toluene or tetrahydrofuran, preferably, dichloromethane, and the solvent of the step (B2) is acetonitrile, dichloromethane, diethyl ether, toluene or tetrahydrofuran, preferably dichloromethane or acetonitrile.

According to one embodiment of the invention, the reaction temperature of the step (B1) and the step (B2) is 0-25° C., preferably, 20-25° C., the reaction time of the step (B1) and the step (B2) is 5-8 h, preferably, 5h.

According to one embodiment of the invention, the molar ratio of the acrylic diester compound represented by the Formula I to the fluorinating agent, boron trifluoride diethyl ether and methyl hydrazine is 1:1:1.0-1.2:1.0-1.1.

The invention provides a method for reacting compound 1 with compound 2, providing a high yield (>80%) of compound 3, and the use of corrosive reagents such as hydrogen fluoride can be reduced with the method.

DESCRIPTION OF THE EMBODIMENTS

The specific embodiments of the present invention will be described in detail below, however, the scope of protection of the present invention is not limited.

Example A1 synthesis of ethylene glycol (3-n, n-dimethylamino)diacrylate

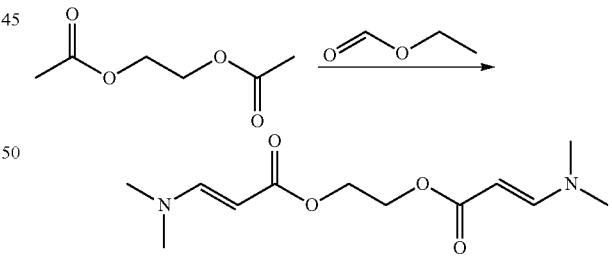

Ethylene glycol diacetate (146 g, 1.0 mol) was dissolved in toluene (800 mL), sodium tert-butoxide (116 g, 1.2 mol) was added, and ethyl formate (89 g, 1.2 mol) was slowly added with stirring. Warmed (room temperature) and stirred overnight to obtain a suspension. The suspension was slowly added to a mixture of dimethylamine hydrochloride (122 g, 1.5 mol) and toluene, and stirred for 2 h. Filtration, the filtrate was washed once with saturated brine (300 mL) and dried with anhydrous sodium sulfate and evaporated to dryness to give pale yellow liquid ethylene glycol bis(3-N, N-dimethylamino) acrylate 216 g, the purity was 98% and the yield was 84%.

Example A2 Synthesis of Hexylene Glycol (3-N,N-dimethylamino) Diacrylate

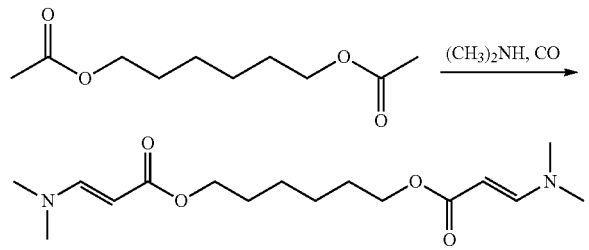

Ethylene glycol diacetate (101 g, 0.5 mol), sodium t-butoxide (120 g, 1.25 mol), toluene (500 mL) was added to the autoclave, the reaction was carried out by introducing co gas at a pressure of 20 bar and a temperature of 60° C. for 4 h, then cooling to room temperature. The reaction solution was slowly added to a mixture of dimethylamine hydrochloride (102 g, 1.25 mol) and toluene (200 mL) in an ice water bath, and reacted for 2 h after room temperature. Filtration, the filtrate was washed with water (300 mL*3), dried with anhydrous sodium sulfate, and evaporated to dryness to give a pale yellow liquid bis(3-N,N-dimethylamino) acrylate 150 g, purity 99%. The rate was 96.1%.

Example A3 Synthesis of Ethylene Glycol (3-N,N-diethylamino)diacrylate

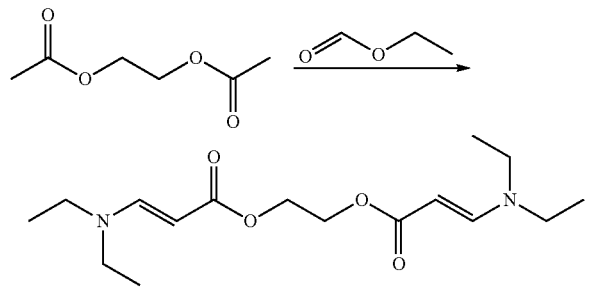

Ethylene glycol diacetate (146 g, 1.0 mol) was dissolved in toluene (800 mL), sodium tert-butoxide (116 g, 1.2 mol) was added, and ethyl formate (89 g, 1.2 mol) was slowly added with stirring. Warmed (room temperature) and stirred overnight to obtain a suspension. The suspension was slowly added to a mixture of diethylamine (109.5 g, 1.5 mol) and toluene, and stirred for 2 h. Filtration, the filtrate was washed once with saturated brine (300 mL) and dried with anhydrous sodium sulfate and evaporated to dryness to give pale yellow liquid ethylene glycol bis(3-N,N-diethyl amino) acrylate 220.4 g, the purity was 98.2% and the yield was 70.6%.

Example A4 Synthesis of Hexanediol (3-N,N-diethylamino) Diacetate

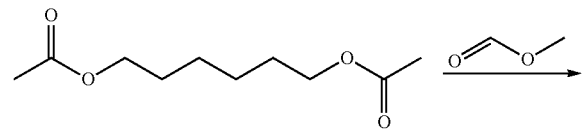

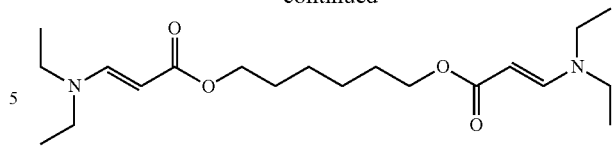

Hexanediol diacetate (101 g, 0.5 mol) was dissolved in toluene (600 mL), potassium tert-butoxide (67.2 g, 0.6 mol) was added, and methylformate (45 g, 0.75 mol) was slowly added with stirring. Warmed (room temperature) and stirred overnight to obtain a suspension. The suspension was slowly added to a mixture of diethylamine ((54.8 g, 0.75 mol) and toluene, and stirred for 2 h. Filtration, the filtrate was washed once with saturated brine (300 mL) and dried with anhydrous sodium sulfate and evaporated to dryness to give pale yellow liquid hexanediol bis(3-N,N-diethylamino) acetate 141.6 g, the purity was 97.3% and the yield was 76.9%.

Example A5 Synthesis of Ethylene Glycol (3-piperidinyl) Diacrylate

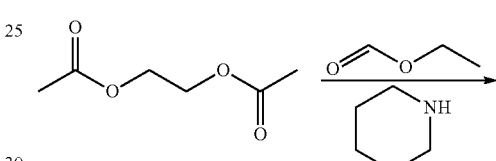

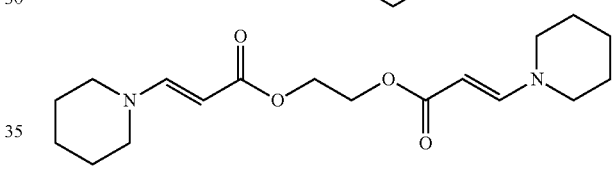

Ethylene glycol diacetate (146 g, 1.0 mol) was dissolved in toluene (800 mL), sodium tert-butoxide (116 g, 1.2 mol) was added, and ethyl formate (89 g, 1.2 mol) was slowly added with stirring. Warmed (room temperature) and stirred overnight to obtain a suspension. The suspension was slowly added to a mixture of piperidine (127.5 g, 1.5 mol) and toluene, and stirred for 2 h. Filtration, the filtrate was washed once with saturated brine (300 mL) and dried with anhydrous sodium sulfate and evaporated to dryness to give pale yellow liquid ethylene glycol bis(3-piperidinyl) acrylate 251.2 g, the purity was 98.6% and the yield was 74.7%.

Example A6 Synthesis of p-phenylene(3-N,N-dimethylamino)diacrylate

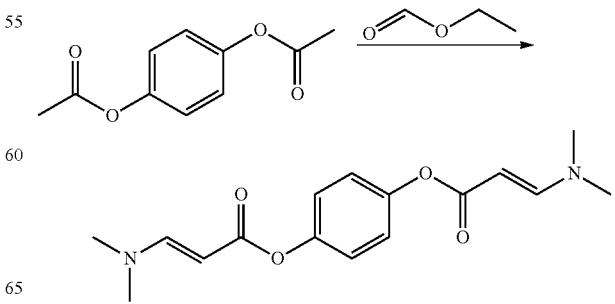

P-phenylenediacetate (97 g, 0.5 mol) was dissolved in toluene (600 mL), sodium tert-butoxide (58 g, 0.6 mol) was added, and ethyl formate (44.5 g, 0.6 mol) was slowly added with stirring. Warmed (room temperature) and stirred overnight to obtain a suspension. The suspension was slowly added to a mixture of dimethylamine hydrochloride (61 g, 0.75 mol) and toluene, and stirred for 2 h. Filtration, the filtrate was washed once with saturated brine (300 mL) and dried with anhydrous sodium sulfate and evaporated to dryness to give pale yellow liquid p-phenylene Bis(3-N,N-dimethylamino) acrylate 86.1 g, the purity was 97.1% and the yield was 56.6%.

Example B1 Synthesis of Ethylene Glycol bis(3-(difluoromethyl)-1-methyl-1h-pyrazole-4-) Carboxylate

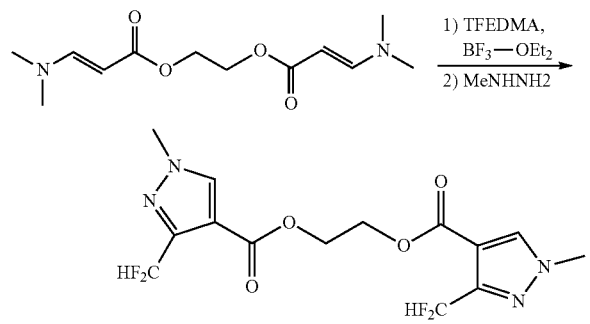

Dichloromethane (400 mL), N,N-dimethyl tetrafluoroethylamine (70 g, 0.48 mol) and boron trifluoride etherate (68.1 g, 0.48 mol) were added to a 1 L three-necked flask, after stirring at room temperature for 30 min, ethylene glycol bis(3-N,N-dimethylamino) acrylate (51.2 g, 0.2 mol) was added and stirring was continued for 2 h. Dichloromethane was removed by evaporation in a water bath at 35° C., methyl hydrazine (23 g, 0.5 mol) was added and stirred at room temperature for 2 h, after concentrating under reduced pressure to remove acetonitrile, hexane (200 mL) was added, and the mixture was stirred at room temperature for 1h, filtered and dried to give pale yellow solid ethylene glycol bis(3-(difluoromethyl)-1-methyl-1h-pyrazole-4-)carboxylate 67.2 g, the purity was 98% and the yield was 89%.

Example B2 Synthesis of Ethylene Glycol bis(3-(difluoromethyl)-1-methyl-1h-pyrazole-4-) Carboxylate Toluene (300 mL), difluoroacetyl fluoride (49 g, 0.44 mol), ethylene glycol bis(3-N,N-dimethylamino) acrylate (51.2 g, 0.2 mol) and triethylamine (60.6 g, 0.60 mol) were added to a 1 L three-necked flask, after stirring at room temperature for 1 h, the reaction solution was slowly added dropwise to a mixture of toluene (100 mL), water (50 mL) and methyl hydrazine (23 g, 0.5 mol) at 0° C., and the reaction was continued for 1 h at 0° C., the toluene layer was separated, washed with water (100 mL*2), dried over anhydrous sodium sulfate and evaporated to remove toluene to give pale yellow solid bis(3-(difluoromethyl)-1-methyl-1h-pyrazole-4-)carboxylate 62 g, the purity was 98.3% and the yield was 82%.

Example B3 Synthesis of Hexanediol bis(3-(difluoromethyl)-1-methyl-1h-pyrazole-4-) Carboxylate

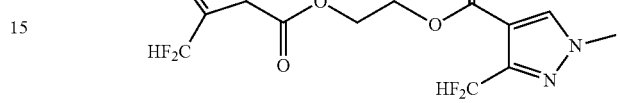

Dichloromethane (600 mL), N,N-dimethyl tetrafluoroethylamine (104.4 g, 0.72 mol) and boron trifluoride etherate (102.2 g, 0.72 mol) were added to a 1 L three-necked flask at room temperature. After stirring for 30 min, bis(3-N,N-dimethylamino) acrylate (93.6 g, 0.3 mol) was added and stirring was continued at room temperature for 2 h. Methylene chloride was removed by evaporation in a water bath at 35° C., and the residue was dissolved in acetonitrile (600 mL), methyl hydrazine (47 g, 1 mol) was added and stirred at room temperature for 2 h, after concentrating under reduced pressure to remove acetonitrile, hexane (500 mL) was added, and the mixture was stirred at room temperature for 1h, filtered and dried to give pale yellow solid bis (3-(difluoromethyl)-1-methyl-1h-pyrazole-4-)carboxylate 112 g, the purity was 99% and the yield was 86%.

Example B4 Synthesis of Ethylene Glycol bis(3-(difluoromethyl)-1-methyl-1h-pyrazole-4-) Carboxylate

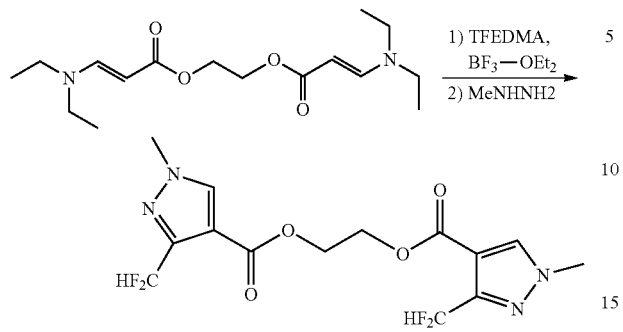

Dichloromethane (400 mL), N,N-dimethyl tetrafluoroethylamine (70 g, 0.48 mol) and boron trifluoride etherate (68.1 g, 0.48 mol) were added to a 1 L three-necked flask at room temperature. After stirring for 30 min, ethylene glycol bis(3-N,N-diethylamino) acrylate (62.4 g, 0.2 mol) was added and stirring was continued at room temperature for 2 h. Methylene chloride was removed by evaporation in a water bath at 35° C., and the residue was dissolved in acetonitrile (300 mL), methyl hydrazine (23 g, 0.5 mol) was added and stirred at room temperature for 2 h, after concentrating under reduced pressure to remove acetonitrile, hexane (200 mL) was added, and the mixture was stirred at room temperature for 1h, filtered and dried to give pale yellow solid bis(3-(difluoromethyl)-1-methyl-1h-pyrazole-4-)carboxylate 57.2 g, the purity was 98%, the yield was 75.6%.

Example B5 Synthesis of Ethylene Glycol bis(3-(difluoromethyl)-1-methyl-1h-pyrazole-4-) Carboxylate

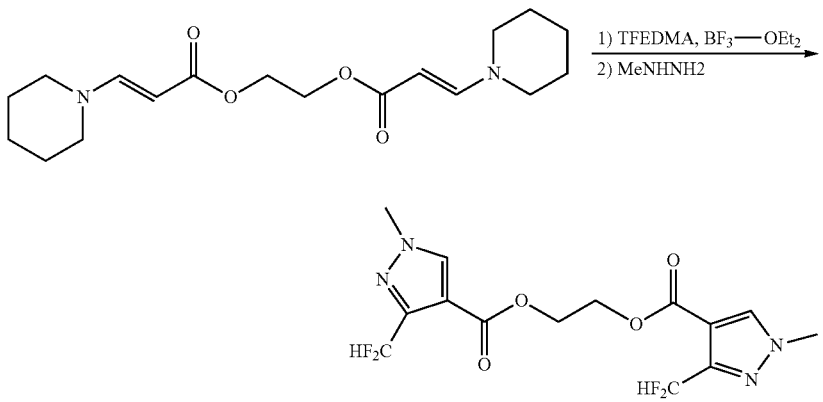

Dichloromethane (400 mL), N,N-dimethyl tetrafluoroethylamine (70 g, 0.48 mol) and boron trifluoride etherate (68.1 g, 0.48 mol) were added to a 1 L three-necked flask at room temperature. After stirring for 30 min, ethylene glycol bis(3-piperidinyl) acrylate (67.2 g, 0.2 mol) was added and stirring was continued at room temperature for 2 h. Methylene chloride was removed by evaporation in a water bath at 35° C., and the residue was dissolved in acetonitrile (300 mL), methyl hydrazine (23 g, 0.5 mol) was added and stirred at room temperature for 2 h, after concentrating under reduced pressure to remove acetonitrile, hexane (200 mL) was added, and the mixture was stirred at room temperature for 1h, filtered and dried to give pale yellow solid bis(3-(difluoromethyl)-1-methyl-1h-pyrazole-4-) carboxylate 45.8 g, the purity was 96.1%, the yield was 60.5%.

Example B6 Synthesis of Benzo(3-(difluoromethyl)-1-methyl-1h-pyrazole-4-)carboxylate

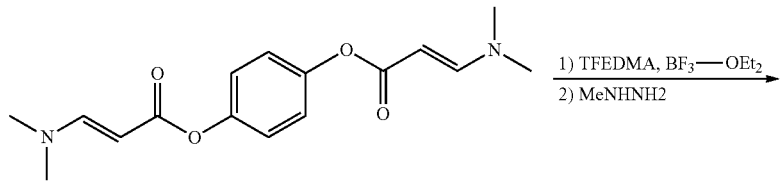

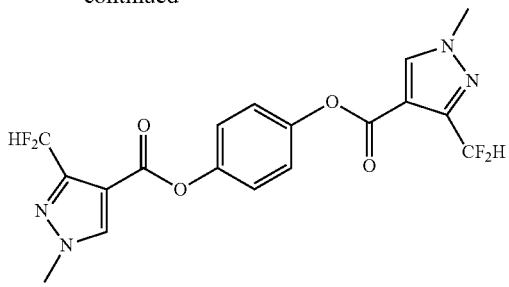

Dichloromethane (400 mL), N,N-dimethyl tetrafluoroethylamine (70 g, 0.48 mol) and boron trifluoride etherate (68.1 g, 0.48 mol) were added to a 1 L three-necked flask at room temperature. After stirring for 30 min, p-phenylene (3-N,N-dimethylamino) acrylate (60.8 g, 0.2 mol) was added and stirring was continued at room temperature for 2 h. Methylene chloride was removed by evaporation in a water bath at 35° C., and the residue was dissolved in acetonitrile (300 mL), methyl hydrazine (23 g, 0.5 mol) was added and stirred at room temperature for 2 h, after concentrating under reduced pressure to remove acetonitrile, hexane (200 mL) was added, and the mixture was stirred at room temperature for 1h, filtered and dried to give pale yellow solid Bis(3-(difluoromethyl)-1-methyl-1h-pyrazole-4-)carboxylate 38.2 g, the purity was 96.1%, the yield was 50.5%.

Example C1 Synthesis of 3-(difluoromethyl)-1-methyl-1h-pyrazole-4-carboxylic Acid

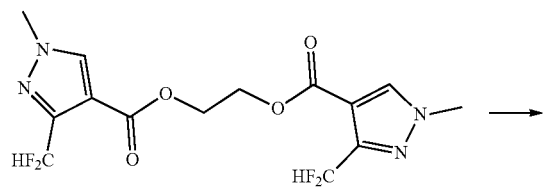

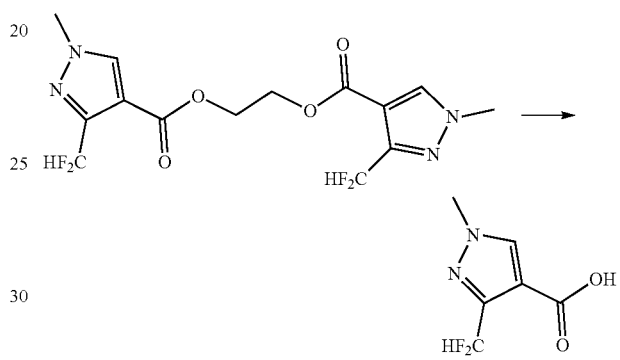

Water (200 mL), methanol (200 mL), sodium hydroxide (10 g, 0.25 mol), ethylene glycol bis(3-(difluoromethyl)-1-methyl-1h-pyrazole-4-) carboxylic ester (37.8 g, 0.1 mol) were added to a 1 L three-necked flask and reacted at 60° C. for 4 hours. After cooling to room temperature, the methanol was removed by concentration under reduced pressure, and then slowly cooled to 0-5° C., stirred for 2 hours, filtered and dried to give a white solid 3-(difluoromethyl)-1-methyl-1h-pyrazole-4-carboxylic acid 32.4 g, the purity was 99.2%, the yield was 92%.

Example C2 Synthesis of 3-(difluoromethyl)-1-methyl-1h-pyrazole-4-carboxylic Acid Water (200 mL), methanol (200 mL), lithium hydroxide monohydrate (10.5 g, 0.25 mol), ethylene glycol bis(3-(difluoromethyl)-1-methyl-1h-pyrazole-4-) carboxylic ester (37.8 g, 0.1 mol) were added to a 1 L three-necked flask and reacted at 60° C. for 4 hours. After cooling to room temperature, the methanol was removed by concentration under reduced pressure, and then slowly cooled to 0-5° C., stirred for 2 hours, filtered and dried to give a white solid 3-(difluoromethyl)-1-methyl-1h-pyrazole-4-carboxylic acid, 31.2 g, the purity was 99.4%, the yield was 88.6%.

Example C3 Synthesis of 3-(difluoromethyl)-1-methyl-1h-pyrazole-4-carboxylic Acid

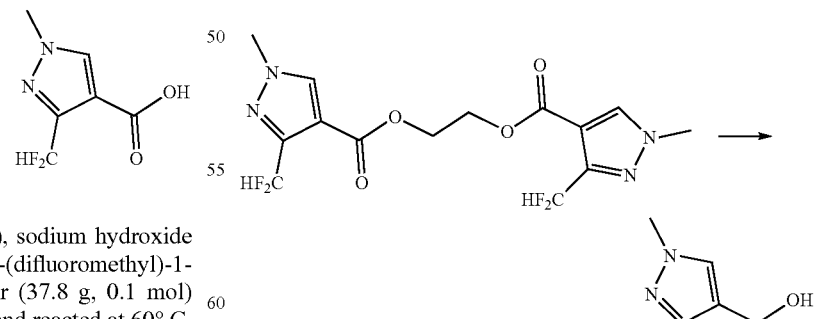

Water (200 m L), methanol (200 m L), potassium hydroxide (18 g, 0.25 mol), ethylene glycol bis(3-(difluoromethyl)-1-methyl-1h-pyrazole-4-) carboxylic ester (37.8 g, 0.1 mol)

were added to a 1 L three-necked flask and reacted at 60° C. for 4 hours. After cooling to room temperature, the methanol was removed by concentration under reduced pressure, and then slowly cooled to 0-5° C., stirred for 2 hours, filtered and dried to give a white solid 3-(difluoromethyl)-1-methyl-1h-pyrazole-4-carboxylic acid, 29.7 g, the purity was 98.6%, the yield was 84.3%.

Example C4 Synthesis of 3-(difluoromethyl)-1-methyl-1h-pyrazole-4-carboxylic Acid

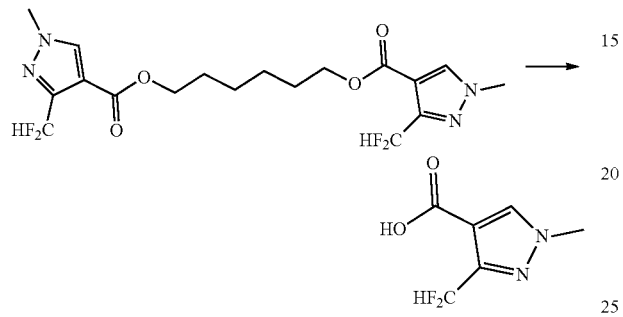

Water (300 m L), methanol (300 m L), sodium hydroxide (15 g, 0.38 mol), hexanediol bis(3-(difluoromethyl)-1-methyl-1h-pyrazole-4-) carboxylate (80 g, 0.18 mol) were added to a 1 L three-necked flask and reacted at 60° C. for 4 hours. After cooling to room temperature, the methanol was removed by concentration under reduced pressure, and then slowly cooled to 0-5° C., stirred for 2 hours, filtered and dried to give a white solid 3-(difluoromethyl)-1-methyl-1h-pyrazole-4-carboxylic acid, 62.5 g, the purity was 99.8%, the yield was 96.3%.

Example C5 Synthesis of 3-(difluoromethyl)-1-methyl-1h-pyrazole-4-carboxylic Acid

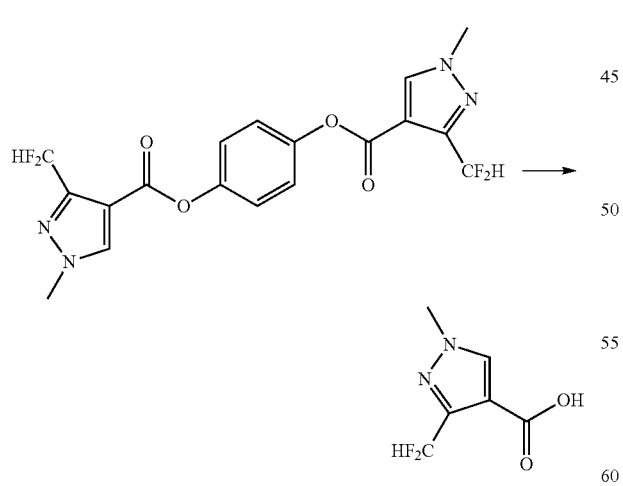

Water (200 mL), methanol (200 mL), sodium hydroxide (10 g, 0.25 mol), ethylene glycol bis(3-(difluoromethyl)-1-methyl-1h-pyrazole-4-) carboxylic ester (42.6 g, 0.1 mol) were added to a 1 L three-necked flask and reacted at 60° C. for 4 hours. After cooling to room temperature, the methanol was removed by concentration under reduced pressure. The residue was diluted with 200 mL of water, extracted with EA (200 m L*2), the aqueous layer was acidified with dilute hydrochloric acid to ph=4, then the aqueous layer was extracted again with EA (200 m L*2), and EA layer was concentrated to dry to give a white solid 3-(difluoromethyl)-1-methyl-1h-pyrazole-4-carboxylic acid 18.6 g, the purity was 98.1%, the yield was 52.8%.

What is claimed is:

1. A method for synthesizing 3-(difluoromethyl)-1-methyl-1h-pyrazole-4-carboxylic acid represented by the following Formula III,

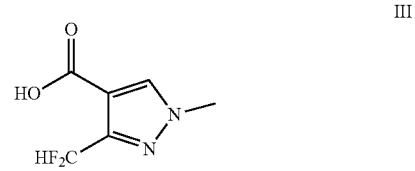

comprising the steps of:

(A) a diethyl ester compound represented by the following Formula IV is reacted under the action of an amine, a base and a carbonylating agent to form an acrylic diester compound represented by the following Formula I,

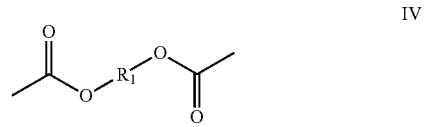

wherein,

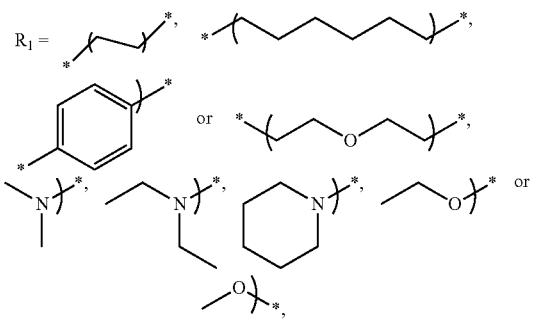

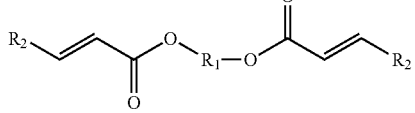

wherein the definition of $R_1$ is the same as above;

(B) the above compound represented by the Formula I is reacted with a fluoride reagent, a Lewis acid and a methyl hydrazine to form a pyrazole ring-containing diester compound represented by the following Formula II,

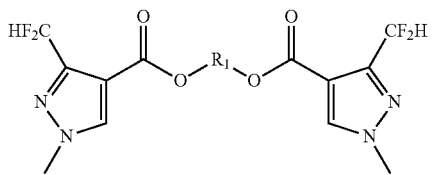

wherein the definition of $R_1$ is the same as above:

(C) a heterocyclic-containing diester compound represented by the Formula II is reacted with a base to form the 3-(difluoromethyl)-1-methyl-1h-pyrazole-4-carboxylic acid represented by the Formula III.

2. The method according to claim 1, wherein the $R_1$ is

and the $R_2$ is

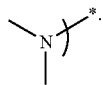

3. The method according to claim 1, wherein the base in the step (C) is an organic base or an inorganic base, the organic base is trimethylamine, triethylamine, ethylenediamine, triisopropanolamine, tripropylamine, imidazole, benzimidazole, 2-fluoropyridine, 4-dimethylaminopyridine, methylpyridine, pyrazine or n-methyldiphenylethylamine, the inorganic base is an alkali metal carbonate or an alkali metal hydroxide.

4. The method according to claim 1, wherein the step (C) is carried out in the presence of a solvent which is water or methanol.

5. The method according to claim 1, wherein the step (A) comprising the steps of:
(A1) the diethyl ester compound represented by the Formula IV is reacted with the carbonylating agent under the action of the base;
(A2) the reaction liquid obtained after the reaction of the step (A1) is reacted with the amine to obtain the acrylic diester compound represented by the Formula I.

6. The method according to claim 1, wherein the step (B) comprising the steps of:
(B1) the acrylic diester compounds represented by the Formula I is reacted with the fluoride reagent and the Lewis acid in solvents;
(B2) the reaction product obtained in step (B1) is reacted with the methyl hydrazine to produce the heterocyclic-containing diester compound represented by the Formula II.

7. The method according to claim 1, wherein the amine in the preparation of the acrylic diester compound is selected from methylamine, dimethylamine, ethylamine, diethylamine, cyclohexylamine, piperidine, morpholine, dimethylamine hydrochloride, diethylamine hydrochloride, cyclohexylamine hydrochloride or piperidine hydrochloride; the base is selected from sodium methoxide, sodium ethoxide, sodium t-butoxide, potassium t-butoxide, sodium hydride or potassium hydride; the carbonylating agent in the preparation of the acrylic diester compound is selected from carbon monoxide, methyl formate, ethyl formate, trimethyl orthoformate or triethyl orthoformate.

8. The method according to claim 1, wherein the fluoride reagent is selected from N,N-dimethyl tetrafluoroethylamine, difluoroacetyl fluoride or difluoroacetyl chloride; the Lewis acid is boron trifluoride etherate.

9. The method according to claim 1, wherein the base in the step (C) is an organic base or an inorganic base, the inorganic base is sodium carbonate, potassium carbonate, sodium hydroxide or potassium hydroxide.

10. The method according to claim 5, wherein the amine in the preparation of the acrylic diester compound is selected from methylamine, dimethylamine, ethylamine, diethylamine, cyclohexylamine, piperidine, morpholine, dimethylamine hydrochloride, diethylamine hydrochloride, cyclohexylamine hydrochloride or piperidine hydrochloride; the base is selected from sodium methoxide, sodium ethoxide, sodium t-butoxide, potassium t-butoxide, sodium hydride or potassium hydride; the carbonylating agent in the preparation of the acrylic diester compound is selected from carbon monoxide, methyl formate, ethyl formate, trimethyl orthoformate or triethyl orthoformate.

11. The method according to claim 6, wherein the fluoride reagent is selected from N,N-dimethyl tetrafluoroethylamine, difluoroacetyl fluoride or difluoroacetyl chloride; the Lewis acid is boron trifluoride etherate.

* * * * *